(12) United States Patent
Jin et al.

(10) Patent No.: US 9,974,445 B2
(45) Date of Patent: May 22, 2018

(54) METHOD, APPARATUS FOR PRESENTING INFORMATION IN A MONITOR AND A MONITOR

(71) Applicant: General Electric Company, Schenectady, NY (US)

(72) Inventors: Wenji Jin, Wuxi (CN); Qingyan Liu, Wuxi (CN); Huan Wang, Wuxi (CN); Yu Ma, Wuxi (CN); Hui Hui, Wuxi (CN); Yuyu Yang, Wuxi (CN); Yongwu Wang, Wuxi (CN); Tao Wang, Wuxi (CN); Xiaoming Guo, Wuxi (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days. days.

(21) Appl. No.: 15/434,323

(22) Filed: Feb. 16, 2017

(65) Prior Publication Data
US 2017/0235904 A1    Aug. 17, 2017

(30) Foreign Application Priority Data
Feb. 16, 2016    (CN) .......................... 2016 1 0086578

(51) Int. Cl.
| | |
|---|---|
| *G08B 23/00* | (2006.01) |
| *A61B 5/021* | (2006.01) |
| *A61B 5/024* | (2006.01) |
| *A61B 5/0402* | (2006.01) |
| *A61B 5/08* | (2006.01) |
| *A61B 5/1455* | (2006.01) |
| *G08B 21/02* | (2006.01) |
| *G08B 31/00* | (2006.01) |

(Continued)

(52) U.S. Cl.
CPC .............. *A61B 5/021* (2013.01); *A61B 5/024* (2013.01); *A61B 5/0205* (2013.01); *A61B 5/0402* (2013.01); *A61B 5/044* (2013.01); *A61B 5/08* (2013.01); *A61B 5/145* (2013.01); *A61B 5/14551* (2013.01); *A61B 5/742* (2013.01); *G08B 21/02* (2013.01); *G08B 31/00* (2013.01); *G16H 40/63* (2018.01)

(58) Field of Classification Search
None
See application file for complete search history.

(56) References Cited

U.S. PATENT DOCUMENTS 4,626,105 A * 12/1986 Miller ...................... A61J 7/04
                                                                  221/2
5,805,051 A *  9/1998 Herrmann ............. A61J 7/0481
                                                                  221/2

(Continued)

*Primary Examiner* — Curtis King

(57) ABSTRACT

The present invention relates to a method and an apparatus for presenting information on a monitor. The method comprising presenting a clock panel according to a range of time at which information to be presented is generated and marking information at a corresponding position on the clock panel according to a time at which the information is generated. The apparatus comprising a clock-panel presenting module for presenting a clock panel according to a range of time at which information to be presented is generated and an information marking module for marking information at a corresponding position on the clock panel according to a time at which the information is generated.

18 Claims, 4 Drawing Sheets

| ECG | SPO2 | NIBP |
|---|---|---|
| total number of warnings within 12 hours:8 | total number of warnings within 12 hours:3 | total number of warnings within 12 hours:6 |
| number of Vtach warnings:2 | SPO2 too low:2 | Systolic blood pressure too high:2 |
| number of Tachy warnings:2 | probe off:1 | Diastolic blood pressure too high:3 |
| number of Brady warnings:4 | | probe off:1 |

(51) Int. Cl.
*A61B 5/00* (2006.01)
*A61B 5/0205* (2006.01)
*A61B 5/044* (2006.01)
*A61B 5/145* (2006.01)

(56) References Cited

U.S. PATENT DOCUMENTS

| | | | | |
|---|---|---|---|---|
| 6,340,242 | B1* | 1/2002 | Sandidge | G04B 37/127 368/223 |
| 6,644,496 | B1* | 11/2003 | Ambrosio | G07F 17/0092 221/124 |
| 7,266,781 | B1* | 9/2007 | Burlowski | G06F 11/1448 704/204 |
| 2001/0040500 | A1* | 11/2001 | Weiner | A61J 7/0481 340/309.7 |
| 2002/0118604 | A1* | 8/2002 | Sharma | G04F 3/02 368/10 |
| 2004/0081023 | A1* | 4/2004 | Ho | A61J 7/0481 368/10 |
| 2006/0007785 | A1* | 1/2006 | Fernandez | G06Q 10/109 368/10 |
| 2006/0018200 | A1* | 1/2006 | Pitocco | G04G 11/00 368/223 |
| 2007/0093719 | A1* | 4/2007 | Nichols, Jr. | A61B 5/02405 600/509 |
| 2009/0046096 | A1* | 2/2009 | Rampersad | G06F 19/3406 345/419 |
| 2009/0109798 | A1* | 4/2009 | West | G09B 23/281 368/10 |
| 2009/0141593 | A1* | 6/2009 | Taha | G01D 7/02 368/10 |
| 2011/0143326 | A1* | 6/2011 | Gurley | G09B 23/28 434/262 |
| 2011/0144528 | A1* | 6/2011 | Gurley | A61B 5/01 600/549 |
| 2011/0194381 | A1* | 8/2011 | Schnabel | G09B 19/12 368/17 |
| 2012/0074683 | A1* | 3/2012 | Gehrki | B42D 15/00 283/81 |
| 2012/0320079 | A1* | 12/2012 | Feddes | G06T 11/206 345/593 |
| 2013/0083029 | A1* | 4/2013 | Vadlamudi | G06F 19/3406 345/440 |
| 2016/0188165 | A1* | 6/2016 | Dixon, III | G06F 19/3487 715/814 |
| 2016/0249831 | A1* | 9/2016 | Eastman | A61B 5/1118 345/440 |
| 2017/0004261 | A1* | 1/2017 | Abou-Hawili | G06F 19/327 |

* cited by examiner

METHOD, APPARATUS FOR PRESENTING INFORMATION IN A MONITOR AND A MONITOR

CROSS-REFERENCE TO RELATED APPLICATIONS

This application claims priority to Chinese patent application number 201610086578.2, filed on Feb. 16, 2016, the entirety of which is incorporated herein by reference.

BACKGROUND

The present invention relates to a method and an apparatus for presenting information, particularly to a method and an apparatus for presenting information on a monitor.

A medically used monitor may monitor multiple types of physiological indexes of a patient. For example, it may measure and record waveforms and parameters related to physiological indexes, such as ECG, SPO2, noninvasive blood pressure (NIBP) and the like of a patient for a long time. When a certain physiological index is abnormal or the monitor itself goes wrong, the monitor will generate a corresponding warning according to preset rules. The warning information is usually stored.

However, when a doctor observes historical warning information, the existing monitor can only present such information in form of text table. In addition, since the text table does not contain a corresponding waveform graph, if the doctor needs to observe the waveform graph, he needs to further take additional operation steps so that the corresponding waveform graph can be found in other places other than the text table.

Accordingly, there is a need to provide a novel method and apparatus for presenting information in a monitor and a corresponding monitor, capable of presenting the information being monitored to the doctor more vividly and more intuitively.

SUMMARY

One embodiment of the present invention provides a method for presenting information in a monitor, comprising: presenting a clock panel according to a range of time at which information to be presented is generated; and marking information at a corresponding position on the clock panel according to a time at which the information is generated.

Another embodiment of the present invention provides an apparatus for presenting information in a monitor, comprising: a clock-panel presenting module for presenting a clock panel according to a range of time at which information to be presented is generated; and an information marking module for marking information at a corresponding position on the clock panel according to a time at which the information is generated.

Yet another embodiment of the present invention provides a monitor, comprising: the apparatus for presenting information in the monitor according to the present invention; and a display screen, which is connected with the apparatus for presenting information in the monitor and used to display the information presented by the apparatus.

BRIEF DESCRIPTION OF THE DRAWINGS

The present invention can be better understood in light of the following description of embodiments of the present invention with reference to the accompanying drawings, in which.

DETAILED DESCRIPTION

Figure 1:
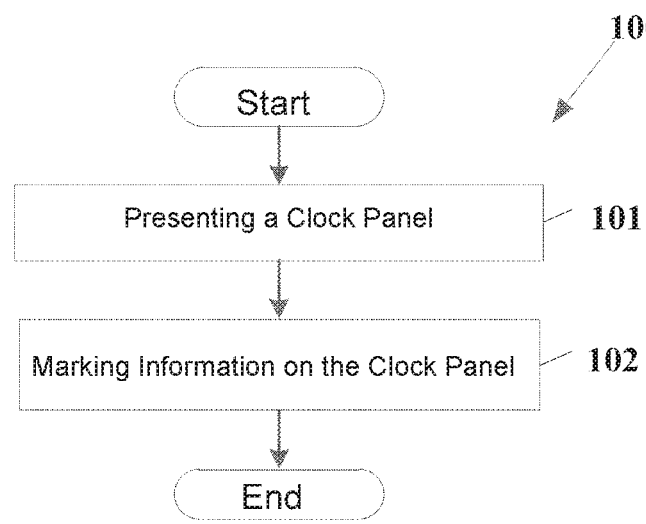
FIG. 1 illustrates a schematic flow chart of one embodiment of a method for presenting information in a monitor of the present invention.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

In order to make the purpose, the technical solutions and the advantages of the invention more apparent, the technical solutions of the present invention will be set forth clearly and fully in the following by combining with specific embodiments of the invention and the corresponding accompanying drawings. Obviously, the described embodiments are merely part—not all—of the embodiments in the present invention. In view of the embodiments in the present invention, other embodiments made by one of ordinary skilled in the art without inventive work all fall within the scope of protection of the invention.

In one embodiment of the present invention, the technical solution of the present invention may be used to present historical warning information stored in a monitor. Although the following embodiments all take historical warning information as examples, an application range of the technical solution of the present invention is not limited thereto, but may also be used to present other information in the monitor, for example, the technical solution of the present invention may also be used to present any information containing a timestamp in the monitor.

In one embodiment of the present invention, information may be presented by displaying the information on a display of the monitor, and may also be presented by printing the information out.

According to the embodiments of the present invention, a method for presenting information in a monitor is provided.

Referring to FIG. 1, which illustrates a schematic flow chart of one embodiment 100 of a method for presenting information in a monitor of the present invention. The embodiment 100 may comprise the following Steps 101 to 102.

As shown in FIG. 1, in Step 101, a clock panel is presented according to a range of time at which information to be presented is generated.

Figure 2:
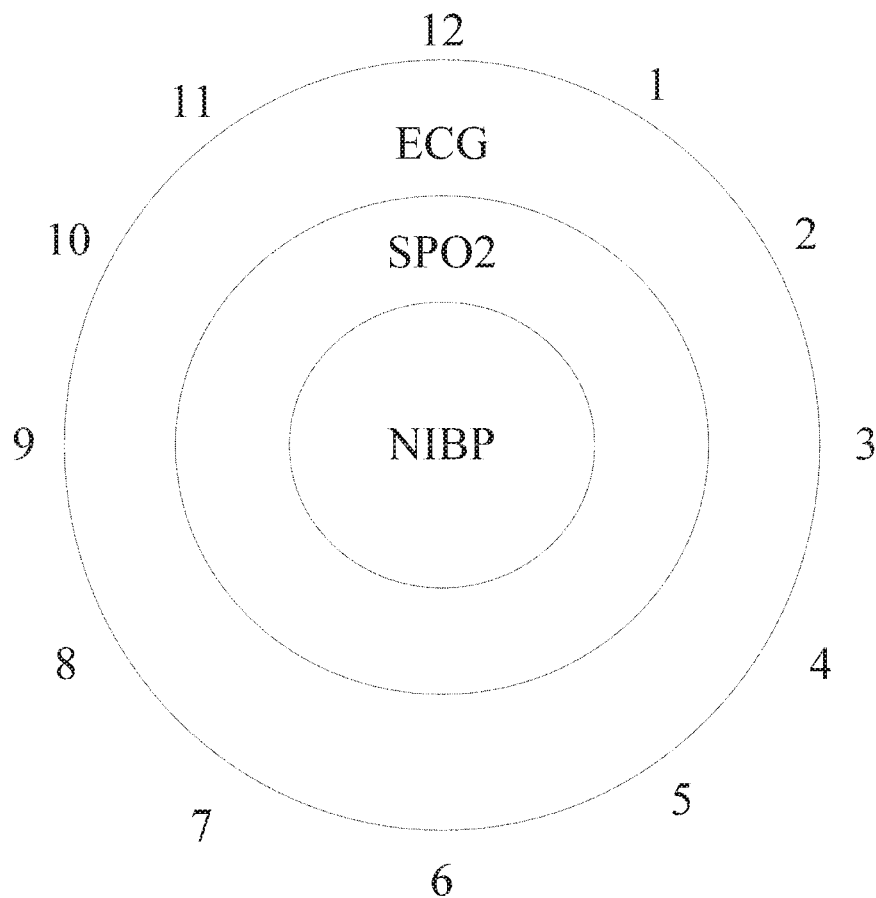
FIG. 2 illustrates a schematic diagram of one embodiment of a clock panel presented by the technical solution of the present invention.

As shown in FIG. 2, the clock panel may be composed of circles and multiple numerical values representing time points. Said numerical values may be distributed evenly at an outer periphery of the circles. Said numerical values may be numbered successively from 1 to 12 just like a watch panel, and may also be numbered with intervals from 1 to 12, for example, may be numbered in a manner of 3, 6, 9, 12 and so on, such that it can be used to present the warning information from 0 o'clock to 12 o'clock.

Furthermore, numbering may also be performed according to a range of time requested to be presented in a request for presenting historical warning information, or according to a preset range of time. For example, if the warning information generated from 0 o'clock to 24 o'clock on a certain day is requested to be presented, then numbers from 1 to 24 may be presented on a circle. If the warning information generated from 22 o'clock last night to 9 o'clock this morning is requested to be presented, then numbers from 22 to 9 may be presented on the circle.

In short, the numerical values on the clock panel are not limited to 1-12 as shown in FIG. 2. The numerical values may be set according to a range of time at which information to be presented is generated.

In one embodiment of the present invention, a plurality of concentric circles may also be presented on the clock panel according to a number of types of the information. For example, the monitor may monitor three types of physiological indexes including ECG, SPO2 and NIBP of a patient, and correspondingly may generate warning information of these three aspects. Then as shown in FIG. 2, three concentric circles may be presented on the clock panel, and a name of information represented by each concentric circle may also be presented within the each concentric circle.

In Step 102, information is marked at a corresponding position on the clock panel according to a time at which the information is generated.

Figure 3:
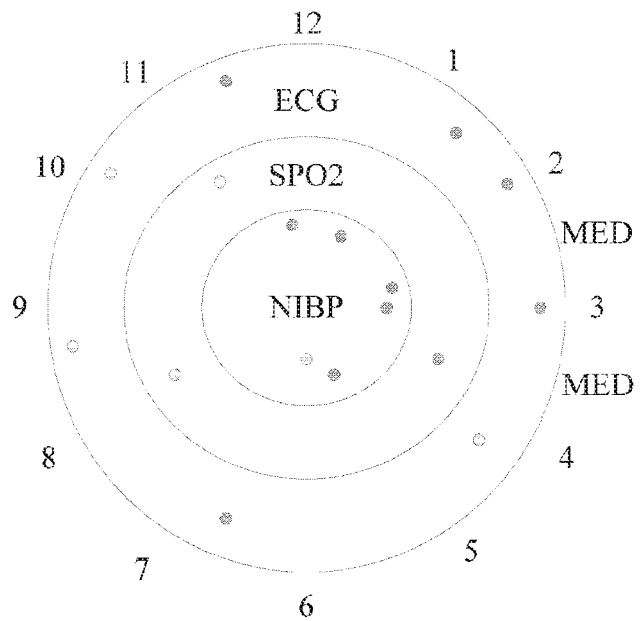
FIG. 3 illustrates a schematic diagram of one embodiment of warning information in the monitor presented by the technical solution of the present invention.

With regard to the stored historical warning data, it will usually include a time at which the warning occurs. Therefore, in one embodiment of the present invention, the warning information may be marked on the corresponding position of the clock panel according to the time at which the warning occurs. For example, as shown in FIG. 3, when a certain piece of warning information is generated at 8:00, one preset identifier may be presented on a direction of 8:00 on the clock panel, for representing the warning information. In one embodiment of the present invention, when the clock panel includes a plurality of concentric circles used to distinguish the types of the warning information, the warning information may be marked within the corresponding concentric circles according to the types of the warning information. For example, when a certain piece of warning information generated at 8:00 belongs to the SPO2 warning, one preset identifier may be presented within the circle where SPO2 resides.

In one embodiment of the present invention, information of different ratings may be marked on the clock panel with different identifiers. Usually, the warning information in the monitor may be classified into several ratings including high, medium, low and the like. Therefore, the warning information of different rating may be marked for displaying on the clock panel with identifiers of different shapes and/or colors. For example, as shown in FIG. 3, a warning of high rating may be represented by a red dot and a warning of medium rating may be represented by a yellow dot.

In one embodiment of the present invention, in order to facilitate the doctor's observation on the change of the patient's physiological index after giving medicine to the patient, medicine time of the patient may also be presented on the outer periphery of the clock panel. For example, as shown in FIG. 3, if medicine is given at 2:30 and 3:30 respectively, then MED may be used at the positions of 2:30 and 3:30 on the outer circumference of the clock panel to represent the medicine time.

So far, one embodiment of the method of the present invention has been described. Said embodiment can present the stored warning information within a period of time in the monitor to the user vividly and intuitively.

Figure 4:
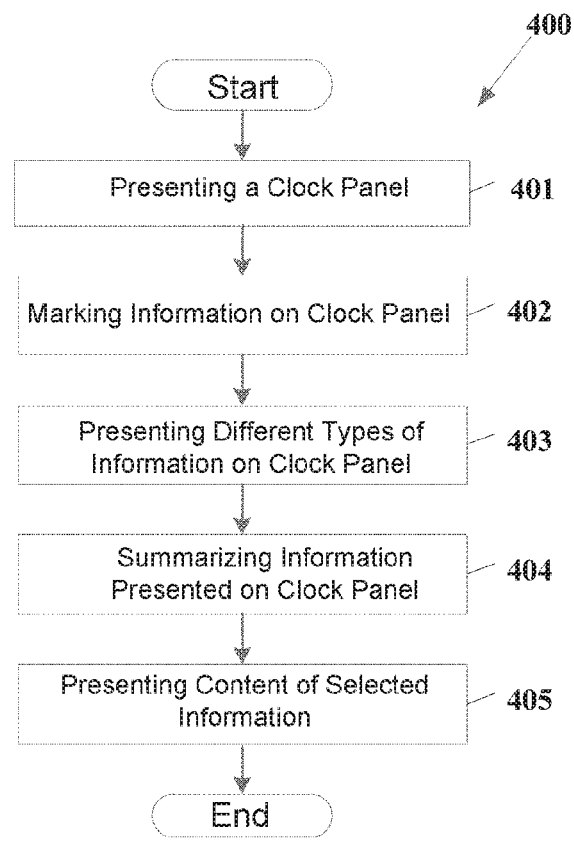
FIG. 4 illustrates a schematic flow chart of another embodiment of a method for presenting information in a monitor of the present invention.

Referring to FIG. 4, which illustrates a schematic flow chart of another embodiment 400 of a method for presenting information in a monitor of the present invention. The embodiment 400 may comprise the following Steps 401 to 405. Steps 401 to 402 therein are similar to the above Steps 101 to 102, which will not be repetitively described herein in details.

In Step 403, a total number of information of different types is presented.

Figure 5:
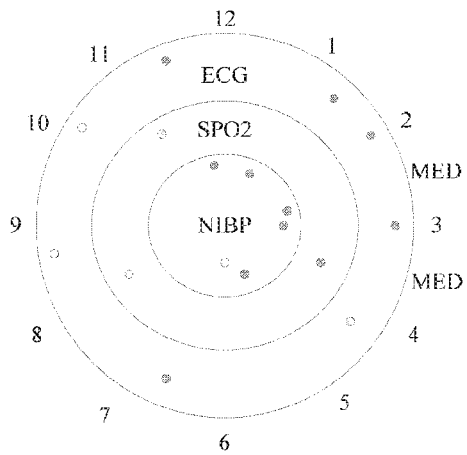
FIG. 5 illustrates a schematic diagram of another embodiment of warning information in the monitor presented by the technical solution of the present invention.

In one embodiment of the present invention, while presenting historical warning information to the user in form of clock panel, as shown in FIG. 5, number of occurrences for each type of warning information may also be counted by type according to the types of the warning information near the clock panel. For example, in FIG. 5, total numbers of warnings of different types may be presented to the user in three rows: one representing ECG warning, one representing SPO2 warning, and one presenting NIBP warning. Taking the ECG warning therein as an example, the total number of the ECG warning information within 12 hours is 8, in which there are two pieces of Vtach warning information, two pieces of Ventricular Tachy warning information, and four pieces of Ventricular Brady warning information.

In Step 404, a summary of information within a selected period of time is presented, when a request for selecting a period of time is received.

In one embodiment of the present invention, when the user selects a certain period of time on the clock panel by an input device (e.g., mouse, keyboard, touch screen and the like), a request for selecting a period of time may be produced. After receiving the request, a summary of the warning information within the period of time selected by the user may be presented to the user.

Figure 6:
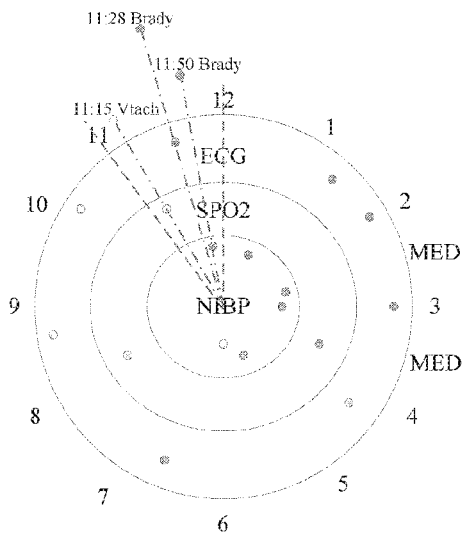
FIG. 6 illustrates a schematic diagram of one embodiment for presenting a summary of warning information within a selected period of time of the technical solution of the present invention.

For example, as shown in FIG. 6, when the user selects a period of time from 11 o'clock to 12 o'clock, summaries of the three pieces of warning information within the period of time may be presented to the user on the positions other than the clock panel. As to what belongs to a summary in warning information, it may be preset or pre-defined by the user. For example, as shown in FIG. 6, a specific time at which warning information is generated and a name of the warning may be presented to the user as a summary.

In Step 405, a content of selected information is presented, when a request for presenting a content of information is received.

Figure 7:
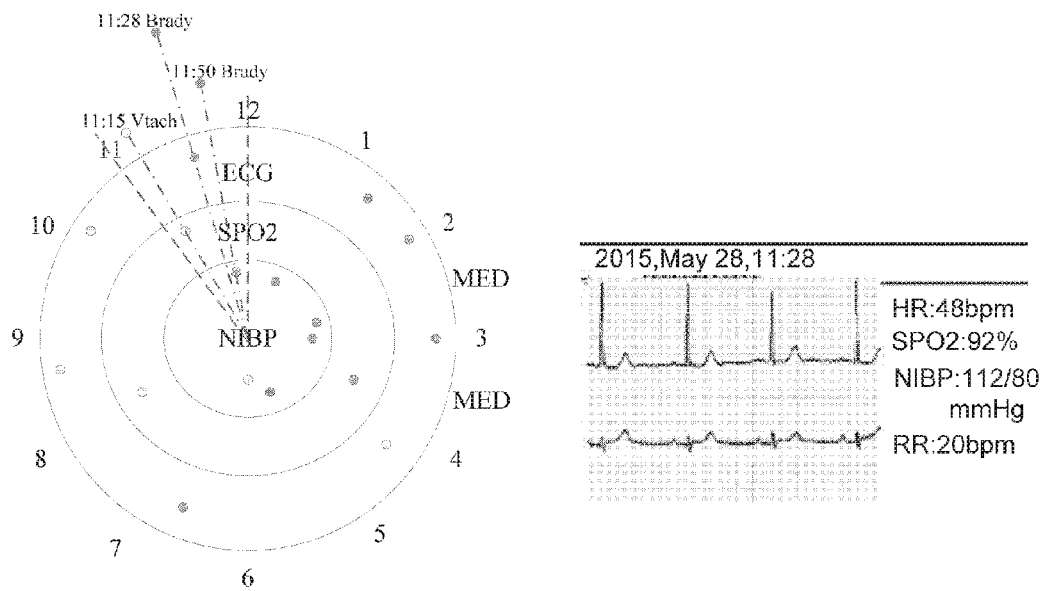
FIG. 7 illustrates a schematic diagram of one embodiment for presenting a content of selected warning information of the technical solution of the present invention.

When the user wishes to know the specific content of one certain piece of warning information in details, he may select a certain warning on the clock panel by the input device (e.g., mouse, keyboard, touch screen and the like), which may produce a request for presenting the content of the information. When receiving said request, the specific content of the warning information may be presented to the user aside the clock panel. As shown in FIG. 7, after the user selects the Brady warning occurring at 11:28, the specific content e.g., ECG waveform graph, heart rate (HR), respiration rate (RR), SPO2 measurement value, NIBP measurement value and the like, of the warning information stored at that time may be presented aside the clock panel.

Figure 8:
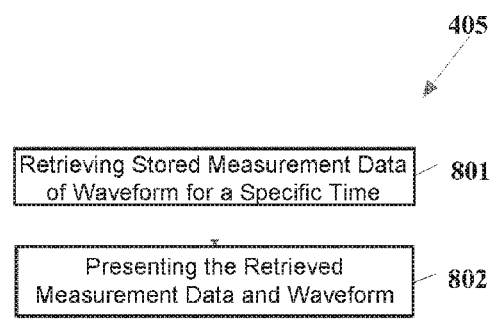
FIG. 8 illustrates a schematic flow chart of one embodiment for presenting a content of the selected information when receiving a request for presenting a content of information during the method for presenting information in the monitor of the present invention.

As shown in FIG. 8, in one embodiment of the present invention, Step 405 may further comprise the following sub-steps 801 to 802.

In sub-step 801, a stored measurement data and waveform are retrieved according to a time at which the selected information is generated.

For example, when the user selects the warning information occurring at 11:28, the measurement data and the waveform graph stored at that time may be retrieved according to said time.

In sub-step 802, the measurement data and waveform are presented.

In one embodiment of the present invention, the measurement data and waveform graphs retrieved in sub-step 801 may all be displayed. In another embodiment of the present invention, only the waveform graph and measurement data closely related to the type of warning may be displayed according to the type of the selected information.

So far, another embodiment of a method for presenting information in a monitor according to the embodiments of the present invention has been described. This embodiment not only can present the stored warning information within a period of time in the monitor to the user vividly and intuitively, but also can display the warning information in summary or in details according to different types of requests issued by the user.

Similar to the above method, the present invention also provides a corresponding apparatus.

Figure 9:
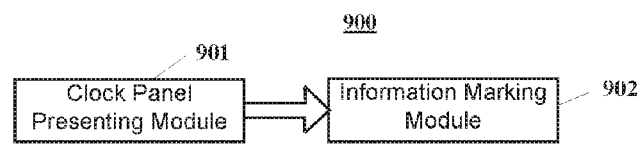
FIG. 9 illustrates a schematic block diagram of one embodiment of an apparatus for presenting information in a monitor of the present invention.

FIG. 9 illustrates a schematic block diagram of one embodiment of an apparatus for presenting information in a monitor of the present invention.

As shown in FIG. 9, the apparatus 900 may comprise: a clock-panel presenting module 901 for presenting a clock panel according to a range of time at which information to be presented is generated; and an information marking module 902 for marking information at a corresponding position on the clock panel according to a time at which the information is generated.

In one embodiment of the present invention, the clock-panel presenting module 901 may further comprise: a concentric-circle presenting module for presenting a plurality of concentric circles on the clock panel according to a number of types of the information.

In one embodiment of the present invention, the information marking module 902 may further comprise: an information-type marking module for marking the information within a corresponding concentric circle according to a type of the information.

In one embodiment of the present invention, the information marking module 902 may further comprise: an information-rating marking module for marking information of different ratings on the clock panel with different identifiers.

In one embodiment of the present invention, the information may comprise medicine time, and the information marking module 902 may further comprise: a medicine-time presenting module for presenting the medicine time on an outer periphery of the clock panel.

In one embodiment of the present invention, the apparatus 900 may further comprise: a total-number-of-information presenting module for presenting a total number of information of different types.

In one embodiment of the present invention, the apparatus 900 may further comprise: an information-within-a-period-of-time presenting module for presenting a summary of information within a selected period of time when a request for selecting a period of time is received.

In one embodiment of the present invention, the apparatus 900 may further comprise: a content-of-information presenting module for presenting a content of selected information when a request for presenting a content of information is received.

In one embodiment of the present invention, the content-of-information presenting module may further comprise: a stored-data searching module for searching for a stored measurement data and waveform according to a time at which the selected information is generated; and a data presenting module for presenting the measurement data and waveform.

So far, an apparatus for presenting information in a monitor according to the embodiments of the present invention has been described. Similar to the above method, the apparatus of the present invention not only can present the stored warning information within a period of time in the monitor to the user vividly and intuitively, but also can display the warning information in summary or in details according to different types of requests issued by the user.

The above descriptions are merely embodiments of the invention and are not intended to restrict the scope of the invention. All kinds of variations and modifications could be made to the present invention to those skilled in the art. Any modifications, alternatives and improvements made within the spirit and principles of the present invention shall fall within the scope of the appended claims.

What is claimed is:

1. A method for presenting information in a monitor, comprising:
    presenting a clock panel according to a range of time at which multiple pieces of warning information to be presented are generated, wherein each piece of warning information is only generated responsive to a physiological index of a patient being abnormal; and
    marking only each piece of warning information at a corresponding position on the clock panel according to a time at which the piece of warning information is generated.

2. The method according to claim 1, wherein the step of presenting a clock panel according to a range of time at which information to be presented is generated further comprises presenting a plurality of concentric circles on the clock panel according to a number of types of the multiple pieces of warning information.

3. The method according to claim 1, wherein the step of marking each piece of warning information at a corresponding position on the clock panel according to a time at which the piece of warning information is generated further comprises marking each piece of warning information within a corresponding concentric circle according to a type of the piece of warning information.

4. The method according to claim 1, wherein the step of marking each piece of warning information at a corresponding position on the clock panel according to a time at which the piece of warning information is generated further comprises marking each piece of warning information on the clock panel based on a rating of the piece of warning information, wherein different ratings correspond to different identifiers.

5. The method according to claim 1, further comprising presenting a medicine time on an outer periphery of the clock panel.

6. The method according to claim 1, further comprising presenting a total number of each type of warning information.

7. The method according to claim 1, further comprising presenting a summary of warning information within a selected period of time when receiving a request for selecting a period of time.

8. The method according to claim 1, further comprising presenting a content of a selected piece of warning information when receiving a request for presenting the content of the selected piece of warning information.

9. The method according to claim 8, wherein the step of presenting a content of a selected piece of warning information when receiving a request for presenting the content of the selected piece of warning information further comprises:
    retrieving a stored measurement data and waveform according to a time at which the selected piece of warning information is generated; and
    presenting the measurement data and waveform.

10. An apparatus for presenting information in a monitor, comprising:
    a clock-panel presenting module for presenting a clock panel according to a range of time at which only multiple pieces of warning information to be presented are generated, wherein each piece of warning information is generated responsive to a physiological index of a patient being abnormal: and
    an information marking module for marking only each piece of warning information at a corresponding position on the clock panel according to a time at which the piece of warning information is generated.

11. The apparatus according to claim 10, wherein the clock-panel presenting module further comprises a concentric-circle presenting module for presenting a plurality of concentric circles on the clock panel according to a number of types of the multiple pieces of warning information.

12. The apparatus according to claim 10, wherein the information marking module further comprises an information-type marking module for marking each piece of warning information within a corresponding concentric circle according to a type of the piece of warning information.

13. The apparatus according to claim 10, wherein the information marking module further comprises an information-rating marking module for marking each piece of warning information on the clock panel based on a rating of the piece of warning information, wherein difference ratings correspond to different identifiers.

14. The apparatus according to claim 10, wherein the information marking module further comprises a medicine-time presenting module for presenting a medicine time on an outer periphery of the clock panel.

15. The apparatus according to claim 10, further comprising a total-number-of-information presenting module for presenting a total number of each type of warning information.

16. The apparatus according to claim 10, further comprising an information-within-period-of-time presenting module for presenting a summary of warning information within a selected period of time when receiving a request for selecting a period of time.

17. The apparatus according to claim 10, further comprising a content-of-information presenting module for presenting a content of a selected piece of warning information when receiving a request for presenting the content of the selected piece of warning information.

18. The apparatus according to claim 17, wherein the content-of-information presenting module further comprises:
    a data retrieving module for retrieving a stored measurement data and waveform according to a time at which the selected piece of warning information is generated; and
    a data presenting module for presenting the measurement data and waveform.

* * * * *